United States Patent [19]

Doyle

[11] 4,269,784

[45] May 26, 1981

[54] PROCESS FOR CONVERTING CO AND $H_2O$ INTO HYDROCARBONS USING WATER-SOLUBLE RUTHENIUM CATALYSTS

[75] Inventor: Gerald Doyle, Bridgewater, N.J.

[73] Assignee: Exxon Research & Engineering Company, Florham Park, N.J.

[21] Appl. No.: 85,106

[22] Filed: Oct. 15, 1979

[51] Int. Cl.$^3$ ............................ C07C 1/02; C07C 1/10
[52] U.S. Cl. ..................................... 518/715; 585/733
[58] Field of Search .................... 260/449 R, 449.6 R; 585/733

[56] References Cited

U.S. PATENT DOCUMENTS

| | | | |
|---|---|---|---|
| 2,632,014 | 3/1953 | Gresham | 260/449 R |
| 2,786,863 | 3/1957 | Kolbel et al. | 260/449.6 |
| 3,055,949 | 9/1962 | Howk et al. | |

FOREIGN PATENT DOCUMENTS

| | | | |
|---|---|---|---|
| 1092458 | 11/1960 | Fed. Rep. of Germany | 260/449.6 |
| 2445193 | 1/1976 | Fed. Rep. of Germany | |
| 2644185 | 4/1977 | Fed. Rep. of Germany | 260/449 R |

OTHER PUBLICATIONS

Kolbel, Die Makromoleinlare Chemie, Bosel, 70 (1964) pp. 1-11.
Halpern et al., J.A.C.S., 83, pp. 4097-4098 (1961).

*Primary Examiner*—Howard T. Mars
*Attorney, Agent, or Firm*—James H. Takemoto

[57] ABSTRACT

A homogeneous process for preparing hydrocarbons from CO and $H_2O$, $D_2O$ or $T_2O$ employing a soluble ruthenium catalyst. The process comprises contacting CO and $H_2O$, $D_2O$ or $T_2O$ in the presence of a homogeneous aqueous solution containing a catalytically effective amount of a water-soluble ruthenium compound and heating the solution to temperatures of from 200° to 500° C. at pressures of from 0.1 to 100 MPa, the products are $C_9$ to $C_{60}$ hydrocarbons.

6 Claims, No Drawings

PROCESS FOR CONVERTING CO AND H₂O INTO HYDROCARBONS USING WATER-SOLUBLE RUTHENIUM CATALYSTS

BACKGROUND OF THE INVENTION

1. Field of the Invention

This invention relates to the synthesis of hydrocarbons from carbon monoxide and water. More particularly, CO and H$_2$O are contacted with a water-soluble ruthenium catalyst in an aqueous solvent.

2. Description of the Prior Art

It is known to convert CO and H$_2$O into hydrocarbons. These reactions, however, are generally heterogeneous since the catalytic system usually involves transition metals in their elemental state.

W. H. E. Mueller and H. Hammer (*Makromol. Chem.*, 70:1-11 (1964)) describe the heterogeneous synthesis of high molecular weight paraffins from carbon monoxide in aqueous suspension of ruthenium metal. High-melting paraffin waxes (up to 131° C., mole wts. up to 7000) are prepared by feeding CO into an aqueous suspension of finely dispersed metallic ruthenium (75-200 atm., 150°-260° C.). Similarly, German Pat. No. 1,092,458 describes the preparation of hydrocarbons and oxygen-containing compounds by the heterogeneous reaction of carbon monoxide with water in the presence of aqueous catalyst suspensions at 180°-300° C. and greater than 4 atmosphere pressure. Catalysts used are Co, Ni or stabilized Fe compounds in suspension. Best results are obtained using suspension of ruthenium catalysts.

J. Halpern, B. R. James and A. L. W. Kemp (*J. Am. Chem. Soc.*, 83:4097-8 (1961)) report the hydration of acetylenic compounds to aldehydes or ketones using ruthenium (III) chloride in aqueous solution to give a reaction which proceeded under mild and apparently homogeneous conditions.

U.S. Pat. No. 3,055,949 teaches the preparation of hydroquinone and quinhydrone by the reaction of acetylene and carbon monoxide in a liquid reaction medium and in the presence of a catalytic amount of a halide, a carbonyl or the acetylacetonate of ruthenium or rhodium. The solvent used may be a hydroxylic compound, i.e., water or an alcohol, a ketonic compound or an ether. The catalyst and the solvent are charged to the reaction vessel and then a metered amount of acetylene is introduced. Carbon monoxide is then introduced to provide at least one mole CO per mole acetylene. Hydroquinone or quinhydrone are recovered.

German Pat. No. 2,445,193 teaches a process for the preparation of diethylketone which comprises reacting ethylene, CO and H$_2$O at 150°-300° C. and 100-350 atm pressure in the presence of an inert solvent such as benzene, toluene, xylene, chlorobenzene, etc., using a Ru halide (hydrate) as catalyst.

It is also known to prepare high molecular weight hydrocarbons from carbon monoxide and hydrogen. U.S. Pat. No. 2,632,014 discloses that high molecular weight polymethylenes can be prepared from the reaction of CO and H$_2$ in the presence of water and a ruthenium catalyst such as ruthenium dioxide, ruthenium metal, ruthenium carbonyls and the ruthenium salts of organic carboxylic acids. The molecular weight of the product can be controlled by adjusting the pH and CO:H$_2$ ratio. Hydrogen is not a reactant in the instant invention.

It is an object of this invention to provide a process based on a homogeneous catalytic system for converting a CO and H$_2$O into hydrocarbons. It is a further object to prepare deuterated or tritiated long-chain hydrocarbons.

SUMMARY OF THE INVENTION

It has been discovered that hydrocarbons can be prepared from CO and H$_2$O by employing a homogeneous ruthenium-containing catalyst. The process for preparing C$_9$ to C$_{60}$ aliphatic hydrocarbons or their deuterated or tritiated derivatives comprises contacting CO and water selected from at least one of the group consisting of H$_2$O, D$_2$O, and T$_2$O in the presence of a homogeneous aqueous solution containing a catalytically effective amount of a water-soluble ruthenium compound and heating the solution to temperatures of from 200° to 500° C. at pressures of from 0.1 to 100 MPa.

The homogeneous process of the invention provides good yields of hydrocarbon mixtures under relatively mild reaction conditions and exhibits higher activity than similar reactions utilizing heterogeneous metal catalysts. If heavy water, i.e., D$_2$O or T$_2$O is substituted for H$_2$O, the instant process produces deuterated or tritiated higher molecular weight hydrocarbons in a single step using inexpensive and easily-handled starting materials.

DETAILED DESCRIPTION OF THE INVENTION

The present process employs ruthenium compounds dissolved in aqueous solution. The ruthenium compounds may be simple salts such as the halides, acetyl acetonate or complex salts of the formula [RuL$_6$]$^n$ where L is a neutral or charged ligand including halide, amine, phosphine, nitric oxide, carbon monoxide, cyanide, aquo, sulfite or mixtures thereof and n is the charge on the complex which can range from $-4$ to $+3$ depending on the oxidation state of the central metal and the charge on the ligand. Examples of complexes are Ru(CO)$_x$Cl$_y$ where x and y are numbers from 1 to 4; [Ru(NH$_3$)$_6$]$^{2+}$, [RuNOCl$_5$]$^{2-}$, [Ru(NH$_3$)$_5$Cl]$^{2+}$, (CO)$_2$($\phi_3$P)$_2$RuCl$_2$, [RuCl$_6$]$^{2-}$ and [RuCl$_5$(H$_2$O)]$^{2-}$. Hydrated ruthenium trichloride, i.e., RuCl$_3$.xH$_2$O is the preferred ruthenium compound. Commercially available ruthenium trichloride is complex mixture of chloro or chlorohydroxo species and "x" is nominally about 3. The concentration of ruthenium compound can range from 0.0001 M to 0.1 M, preferably from 0.001 M to 0.01 M.

The solvent system for the reaction is preferably water. Since H$_2$O (or D$_2$O or T$_2$O) is also a reactant, the amount of water is not critical. Organic solvents such as ethers which are miscible with water and not reactive under the reaction conditions may be added, if desired.

The reaction is preferably run at a CO partial pressure of from 1 to 50 MPa, most preferably 5 to 20 MPa. The preferred reaction temperatures are from 200° to 400° C., especially 250° to 350° C.

A continuous or batch process may be employed. Generally, the ruthenium compound is dissolved in water and added to a pressure reactor. The reactor is pressurized with CO, and then heated to the desired temperature. The reactor is agitated during the reaction. Reaction periods may range from 0.1 to 10 hours. After an appropriate time, the reactor is cooled and the product isolated by conventional means such as filtration.

The products of the present process are $C_9$ to $C_{60}$ hydrocarbons and are characterized as predominantly saturated straight chain oils and waxes. The typical product is a paraffin wax which is at least 95% linear and saturated. The products exhibit a range of molecular weights, the particular molecular weight distribution being primarily dependent on the temperature. The molecular weights are inversely related to temperature, i.e., the average molecular weight decreases with increasing temperature. For example, at 250° C., $C_{30}$ to $C_{40}$ products are expected to predominate whereas at 350° C., mostly $C_{12}$ to $C_{22}$ products are obtained.

The process of the invention may be used to prepare fully deuterated or tritiated waxes by employing $D_2O$ or $T_2O$ as solvent and reactant. The degree of deuteration or tritiation in a product can be controlled by regulation of the $H_2O:D_2O$ or $H_2O:T_2O$ ratio. Since the present catalytic reaction does not demonstrate a significant isotope effect, the above isotope ratios will approximate closely the H:D or H:T ratio in the product.

It has been observed that Ru metal is generally recovered at the end of the reaction. In order to distinguish the present invention from a heterogeneous process catalyzed by Ru metal, three comparative experiments were run. In a first test, the product (wax) was removed from the reactor which was immediately recharged with CO and heated. The second test involved isolating the Ru metal obtained after completion of the original reaction and using this as catalyst in second reaction. Finally, Ru metal was specially prepared by a process which gives a large surface area and the metal was not previously exposed to the instant reaction. In all cases, the results obtained were significantly worse than those obtained from a homogeneous process starting with $RuCl_3$. Under identical conditions of temperature and pressure, the homogeneous process produced at least a 10-fold greater amount of wax compared to Ru metal.

Paraffins are useful as water-repellants, sealants, cosmetics, lubricants, candles and the like.

The process of the invention is further exemplified in the following examples.

EXPERIMENTAL

Analysis. All gases, liquids and solids were analyzed by gas chromatography on a Perkin-Elmer Model 900 instrument. Gases and aqueous solutions were analyzed on a chromosorb 102 packed column. Waxes were analyzed on a SE30 packed column. The waxes were analyzed for unsaturation and linearity by gas chromatography-mass spectroscopy. The deuterium content of the deuterated waxes was also determined by mass spectroscopy.

EXAMPLE 1

0.2 g $RuCl_3.xH_2O$ was purchased from Englehard Industries and dissolved in 20 ml $H_2O$ contained in a glass liner. The liner was placed in a 70 ml autoclave which was sealed and pressurized to 2 MPa pressure with CO. The autoclave was heated to 300° C. and stirred for 4 hours. The reactor was then cooled. A gas sample was taken and the autoclave vented and opened. Approximately 0.05 g of solid wax was physically removed from the aqueous mixture. The wax was >90% straight chain saturated hydrocarbons with an average carbon number of about 30. Analysis of the products showed the total conversion of CO was >85%. Small amounts of $CH_4$ and $H_2$ were also formed.

EXAMPLE 2

A 70 ml autoclave was charged 20 ml $D_2O$ and 0.3 g $RuCl_3.(D_2O)_x$ (contained in a Pyrex glass liner) and 2 MPa CO. $RuCl_3.(D_2O)_x$ was prepared by recrystallizing $RuCl_3.(H_2O)_x$ from $D_2O$ containing DCl. The autoclave was then heated with stirring to 250° for six hours and was then cooled. The gas pressure was vented and the autoclave was opened. The product in the glass liner consisted of a small wax button floating on the surface of the unreacted $D_2O$ and some grey Ru metal at the bottom of the tube. The wax was removed and washed with methanol and dried. The dried button weighed 60 mg. The product contained only trace amounts of normal hydrogen and by mass spectral analysis appeared to be mainly a mixture of linear saturated hydrocarbons with an average carbon number of approximately 23. A GC analysis of the gas showed that the conversion was approximately 80% based on CO and that small amounts of $D_2$ and $CD_4$ were also formed in this reaction.

EXAMPLE 3

The procedure of Example 1 was repeated with 0.3 g of $RuCl_3.xH_2O$ and varying temperatures and pressures. After the reaction had cooled, the solid material (wax+Ru metal) was filtered and the wax extracted with hot toluene. The autoclave, liner and other parts were also extracted with hot toluene. The toluene extracts were combined and wax recovered by evaporating the toluene or precipitating the wax by adding methanol. Deuterated waxes were prepared by substituting $D_2O$ for $H_2O$. Ru metal and Ru complexes were also tested. The Ru metal was synthesized by reduction of a solution of $RuCl_3.xH_2O$ with hydrazine, hydrochloride or alternately with sodium borohydride. $CsRu(CO)_3Cl_3$ and $[Ru(CO)_2Cl_2]_2$ are prepared by methods described in *J. Chem. Soc. A*, (1969) Page 372 and *Chem. Ber.*, 57:2130 (1924), respectively.

The results are summarized in Table 1.

TABLE 1

| | Wax Formation from CO and $H_2O$ | | | | |
|---|---|---|---|---|---|
| Example No. | Catalyst | Solvent | Initial CO Press | Temperature | Approximate Wax Yield |
| 1 | $RuCl_3 \cdot \times H_2O$ (0.3g) | $H_2O$ | 300# | 250° | 20 mg. |
| 2 | $RuCl_3 \cdot \times H_2O$ (0.3g) | $H_2O$ | 300# | 260° | 50 mg. |
| 3 | $RuCl_3 \cdot \times H_2O$ (0.3g) | $H_2O$ | 300# | 270° | 50 mg. |
| 4 | $RuCl_3 \cdot \times H_2O$ (0.3g) | $H_2O$ | 250# CO 100# $H_2$ | 250° | 60 mg. |
| 5 | $RuCl_3 \cdot \times H_2O$ (0.3g) | $D_2O$ | 250# CO | 250° | 60 mg. |
| 6 | Ru metal (0.3) | $H_2O$ | 300# | 270° | <5 mg. |

TABLE 1-continued

Wax Formation from CO and H$_2$O

| Example No. | Catalyst | Solvent | Initial CO Press | Temperature | Approximate Wax Yield |
|---|---|---|---|---|---|
| 7 | RuCl$_3$· × H$_2$O(0.3g) | H$_2$O | 1450# | 250° | 100 mg. |
| 8 | RuCl$_3$· × H$_2$O(0.3g) | H$_2$O | 1400# | 340° C. | 300 mg. |
| 9 | RuCl$_3$· × H$_2$O(0.3g) | D$_2$O | 1400# | 340° C. | 270 mg. |
| 10 | CsRu(CO)$_3$Cl$_3$(.2g) | H$_2$O | 400# | 260° | 15 mg. |
| 11 | [Ru(CO)$_2$Cl$_2$]$_2$(.1g) | H$_2$O | 400# | 260° | 5 mg. |
| 12 | FeCl$_3$(.25g) | H$_2$O | 300# | 260° | 0 |
| 13 | NiCl$_2$(.2g) | H$_2$O | 300# | 260° | 0 |
| 14 | CoCl$_2$(.2g) | H$_2$O | 300# | 260° | 0 |

By comparing experiments 3 and 6, it can be seen that under identical reaction conditions, a RuCl$_3$.xH$_2$O solution produced 50 mg of wax whereas Ru metal produced less than 5 mg wax. A comparison of Examples 1, 2, 7 and 8 demonstrates that the reaction is dependent on both the reaction temperature and CO pressure, high temperatures and pressures generally favoring increased yield product.

EXAMPLE 4

This experiment was carried out to show that formation of the hydrocarbons is not due solely to the presence of the insoluble residue containing Ru metal which forms when one carries out this reaction with aqueous solutions of RuCl$_3$.

An autoclave fitted with a glass liner was charged with a solution containing 0.3 g RuCl$_3$.H$_2$O in 20 ml water. The autoclave was sealed and pressurized to 300# with CO. It was then heated to an internal temperature of approximately 220° for six hours. The autoclave was cooled to room temperature, vented, and opened. The waxy material floating on the aqueous layer was removed, dried and weighed, and was found to weigh 50 mg. The autoclave was resealed and repressurized with 300# CO, heated to 220° for an additional six hours and then cooled, vented and opened. In this case, no waxy material was observed. In order to detect any small amounts of hydrocarbon material, the aqueous layer was extracted with carbon tetrachloride and the liner and inside of the autoclave were washed with hot CCl$_4$. The CCl$_4$ extracts and washes were analyzed by gas chromatography but no hydrocarbon fractions could be observed. Evaporation of the CCl$_4$ solution under vacuum gave a residue of less than 5 mg.

What is claimed is:

1. A process for preparing C$_9$ to C$_{60}$ aliphatic hydrocarbons or their deuterated or tritiated derivatives which comprises:
   contacting CO and water selected from at least one of the groups consisting of H$_2$O, D$_2$O, and T$_2$O in the presence of a homogeneous aqueous solution containing a catalytically effective amount of water-soluble ruthenium compound selected from the group consisting of ruthenium halide, ruthenium acetyl acetonate and a complex salt of the formula (RuL$_6$)$^n$ where L is halide, amine, phosphine, nitric oxide, carbon monoxide, cyanide, aquo, sulfite or mixtures thereof and n is a number from −4 to +3; and
   heating the solution to temperatures of from 200° to 500° C. at pressures of from 0.1 to 100 MPa.

2. The process of claim 1 wherein the ruthenium compound is hydrated ruthenium trichloride.

3. The process of claim 1 wherein the concentration of ruthenium compound is from 0.0001 M to 0.1 M.

4. The process of claim 1 wherein the pressure is from 5 to 20 MPa.

5. The process of claim 1 wherein the temperature is from 200° to 350° C.

6. A process for preparing C$_9$ to C$_{60}$ aliphatic hydrocarbons or their deuterated or tritiated derivatives which comprises:
   contacting CO and water selected from at least one of the groups consisting of H$_2$O, D$_2$O, and T$_2$O in the presence of a homogeneous aqueous solution containing a catalytically effective amount of ruthenium trichloride; and
   heating the solution to temperatures of from 200° to 500° C. at pressures of from 0.1 to 100 MPa.

* * * * *